United States Patent
Talton (10) Patent No.: US 7,153,272 B2
(45) Date of Patent: Dec. 26, 2006

(54) METHODS OF COLLECTING AND ANALYZING HUMAN BREATH

(75) Inventor: James D. Talton, Gainesville, FL (US)

(73) Assignee: Nanotherapeutics, Inc., Alachua, FL (US)

( * ) Notice: Subject to any disclaimer, the term of this patent is extended or adjusted under 35 U.S.C. 154(b) by 0 days.

(21) Appl. No.: 10/502,950

(22) PCT Filed: Jan. 29, 2003

(86) PCT No.: PCT/US03/01065

§ 371 (c)(1),
(2), (4) Date: Nov. 18, 2004

(87) PCT Pub. No.: WO03/064994

PCT Pub. Date: Aug. 7, 2003

(65) Prior Publication Data

US 2005/0065446 A1    Mar. 24, 2005

Related U.S. Application Data

(60) Provisional application No. 60/352,322, filed on Jan. 29, 2002.

(51) Int. Cl.
*A61B 5/08* (2006.01)
(52) U.S. Cl. ...................... 600/543; 600/532
(58) Field of Classification Search ............... 600/543
See application file for complete search history.

(56) References Cited

U.S. PATENT DOCUMENTS

| | | | |
|---|---|---|---|
| 4,759,210 A * | 7/1988 | Wohltjen | 73/31.07 |
| 5,081,871 A | 1/1992 | Glaser | |
| 5,469,369 A * | 11/1995 | Rose-Pehrsson et al. | 702/27 |
| 5,479,815 A * | 1/1996 | White et al. | 73/23.3 |
| 5,705,735 A | 1/1998 | Acorn | |
| 5,826,577 A * | 10/1998 | Perroz et al. | 600/532 |
| 6,148,657 A * | 11/2000 | Satoh et al. | 73/23.35 |
| 6,234,006 B1 * | 5/2001 | Sunshine et al. | 73/29.01 |
| 6,244,096 B1 * | 6/2001 | Lewis et al. | 73/23.2 |
| 6,428,483 B1 | 8/2002 | Carlebach | |
| 6,609,068 B1 * | 8/2003 | Cranley et al. | 702/24 |
| 6,726,637 B1 * | 4/2004 | Phillips | 600/543 |

* cited by examiner

*Primary Examiner*—Charles A Marmor, II
*Assistant Examiner*—Patricia Mallari
(74) *Attorney, Agent, or Firm*—Finnegan Henderson Farabow Garrett & Dunner L.L.P.

(57) ABSTRACT

The present invention provides methods of collecting and detecting compounds in a human breath sample, comprising: exhaling into a handheld sample collector to absorb at least one breath compound in an exhaled breath collector of said collector; connecting the handheld sample collector to a breath analyzer; transferring the breath compounds from the exhaled breath collector of the sample collector into the breath analyzer; and detecting breath compounds using two or more sensors. The method may be performed to detect breath compounds for determining health or disease diagnosis, or for drug monitoring.

12 Claims, 5 Drawing Sheets

METHODS OF COLLECTING AND ANALYZING HUMAN BREATH

RELATED APPLICATIONS

The present application claims priority under 35 U.S.C. § 119 to U.S. Provisional Patent Application No. 60/352,322, filed Jan. 29, 2002. The entire content of the aforementioned application is specifically incorporated herein by reference.

BACKGROUND OF THE INVENTION

1. Field of the Invention

The invention relates to methods for collecting and analyzing exhaled breath samples for trace compounds, and devices, apparatuses, and systems for performing such methods.

2. Description of Related Art

Exhaled breath of individuals with some diseases contains distinctive gases, or alveolar gradients compared to air, which differs markedly from the exhaled breath of healthy individuals, i.e. acetone in the breath of individuals with diabetes (Phillips 1992). In addition, because of the high systemic blood flow to the lungs, ingested substances and/or therapeutic drugs are able to partition across the liquid/gas interface and exhaled proportional to systemic levels, i.e. alcohol. Detection of inflammatory markers in the diagnosis of several pulmonary diseases, such as asthma and chronic obstructive pulmonary disease (COPD), could substantially improve the understanding of the pathogenesis of these diseases, improve diagnosis, and identify the efficacy of different therapies. Although progress over the last decade has improved monitoring of forced expiratory volume (FEV) and spirometry, as well as exhaled carbon dioxide and nitric oxide (Montuschi, Kharitonov et al. 2001), these markers tend to vary greatly from patient to patient. Preliminary studies measuring levels of recently identified inflammatory markers in the exhaled breath such as ethane and 8-isoprostane using gas chromatography/mass spectrometry (GC/MS) has shown higher magnitude differences in exhaled levels of COPD patients (ethane 2.77+/−0.25 ppb and 8-isoprostane 40+/−3.1 pg/ml in breath condensate) compared to healthy patients (ethane 0.88+/−0.09 ppb and 8-isoprostane 10.8+/−0.8 pg/ml in breath condensate), suggesting exhaled volatile organic compounds (VOCs) may provide improved markers of COPD and other conditions compared to exhaled NO, $CO_2$, and $H_2O_2$ (Montuschi, Collins et al. 2000; Paredi, Kharitonov et al. 2000). Exhaled VOC profiles have provided a link to other diseases where high levels of oxidative stress markers are present, including lung cancer, liver disease, inflammatory bowel disease, rheumatoid arthritis, and schizophrenia (Phillips, Erickson et al. 1995; Phillips, Herrera et al. 1999; Phillips, Cataneo et al. 2000). Results of several studies have also shown that *Pseudomonas, Klebsiella pneaumoniae, Proteus mirabolis, Staphylococcus aureus, Enterococcus, Clostrdium*, and *E. coli* emit volatile compounds into the headspace of cultures, also suggesting that diagnosis of patients with these diseases could be performed from monitoring compounds in the breath (Larsson, Mardh et al. 1978; Labows, McGinley et al. 1980; Pons, Rimbault et al. 1985; Zechman, Aldinger et al. 1986; Yu, Hamilton-Kemp et al. 2000; Aathithan, Plant et al. 2001).

Unfortunately, progress in breath testing for various diseases and drug monitoring is hindered by the technical difficulty of detecting very low concentrations of exhaled compounds in the breath (nanomolar or picomolar concentrations). Research has been reported using breath sampling using large heated tubes (Phillips 1995) and cylindrical (Lewis, Severin et al. 2001) containers to collect desired portions of the breath for sampling. Unfortunately, these systems require power for pumping and temperature control limiting their widespread use. Detection of compounds in the collected breath sample has been described using gas chromotography coupled with mass spectrometry (GC/MS), which are sensitive and selective but also bulky and complicated, as well as polymer-coated resistor arrays, which have low sensitivity and are not selective with complex mixtures such as the breath, have both been described (Phillips 1997; Lewis, Severin et al. 2001). In addition, a GC system for detection of volitile compounds in the breath has also been described with improved sensitivity and selectivity that utilizes breath collection on a absorbent sample tube and a second chromatography column for separation of compounds (Satoh, Yanagida et al. 2002). Unfortunately, though, there are no currently available portable vapor or gas sensor systems that can collect and detect mixtures of volatile compounds at low levels in breath, as well as separate compounds from the large exhaled water content. What is desired is an optimized sample collection system and superior detection capabilities. In addition, it would be beneficial if sample collection system and the detection system were small in size, ideally hand-held or portable, without compromising sensitivity and selectivity of the compound of interest for detection.

SUMMARY OF THE INVENTION

Features and Advantages of the Invention

The present invention overcomes these and other inherent deficiencies in the prior art by providing novel breath sample collection and detection methods for use in health or disease diagnosis, as well as drug monitoring. In general, the methods disclosed herein provide a means for detecting and quantifying one or more compounds of interest in the exhaled breath from a collected sample.

The described processes have the advantages of producing reliable results from the described system while being portable and requiring minimal energy and space. The invention relates to the discovery that exhalation can be performed directly onto a sorbent phase, without the use of large collection tubes and heating equipment, and efficiently capture breath compounds for analysis. In addition, the use of desorbing captured breath compounds onto a first sorbent phase into a second thermal desorption column with detection using small, inexpensive vapor sensors has not previously been described. First, the sample must be collected onto a sorbent trap before analysis to extract compounds of interest over several breaths. It is desirable that a sample collector (SC) be portable, preferably a small handheld device similar to an asthma drug inhaler, that may be used to collect breath samples from patients and then processed on a central detection system. It is also desirable that the SC collect several breaths only the alveolar breath from the alveoli of the lungs, which contains the volatile compounds of interest, which are present in the lung or have diffused from the blood, and not collect the 'anatomical deadspace' originating from the pharynx, trachea and bronchial tree where no gaseous interchange occurs. Finally, since the content of the environmental air may contain low concentrations of the compounds of interest, it would also be desirable if a sample of the air that is inhaled may be collected onto a sorbent trap in a similar manner for comparison.

For detection, a portable, robust detection system that extracts a gas sample from the concentrated breath and air samples as desired as an alternative to conventional GC/MS systems which are complicated and bulky. An ideal alternative would be a handheld chemical sensor, similar to an electronic nose, which are commercially-available for the detection of chemical spills and volatile organic compounds (VOC's). Unfortunately, these sensor arrays alone may only be used to detect high concentrations of volatile compounds (milli-molar) with reduced sensitivity under high humidity conditions such as the exhaled breath. An improved sensor system with high sensitivity, coupled with a breath sample collector, which can be used to recognize simple and/or complex gas mixtures for a variety of exhaled compounds would be a great benefit to the medical field.

The process also has several advantages over previously described breath collection and analysis techniques including:
1. Portable: the breath collection apparatus allows for collection of the breath sample in any environment, i.e., on the battlefield or in an emergency room.
2. User-friendly: the breath collection apparatus is easy to operate and presents no significant resistance to sampling via inhalation and exhalation. In addition, the detection system processes the sample and provides the desired response in an easy-to-operate interface.
3. Disposable: the breath collection apparatus provides no possible exposure to cross-contamination or exposure to infectious pathogens from another patient.
4. Efficient sampling: The breath collection apparatus can control the breath sampling by collecting only the alveolar breath component, not the dead space.
5. Concentration of sample: The breath collection apparatus may allow for the alveolar breath to be sampled over multiple breaths, thus improving the possibility of detecting compounds of interest that are present at extremely low concentrations in the breath.

SUMMARY OF THE INVENTION

The present invention provides methods of collecting and detecting compounds in a human breath sample, comprising: exhaling into a handheld sample collector to absorb at least one breath compound in an exhaled breath collector of said handheld sample collector; connecting the handheld sample collector to a breath analyzer; transferring the breath compounds from the exhaled breath collector of the sample collector into the breath analyzer; and detecting breath compounds using two or more sensors. The method may be performed to detect breath compounds for determining health or disease diagnosis, or for drug monitoring.

The exhaling may comprise multiple exhaled breaths into the exhaled breath collector of the sample collector, and may contain at least one sorbent phase to absorb breath compounds. The sorbent phase is selected from, but not limited to, activated carbon, silica gel, activated alumina, molecular sieve carbon, molecular sieve zeolites, silicalite, $AlPO_4$, alumina, polystyrene, and combinations thereof. The handheld sample collector may further comprise inhaling through an outside, or environmental, air collector, which may precede exhaling into the exhaled breath collector. The first portion of the exhaled breath may bypass the exhaled breath collector.

The sample collector may be placed in fluid communication with a breath analyzer system, and the breath analyzer may separate the breath compounds using a thermal desorption column.

Detection may be performed using mass spectroscopy, or electronic, optical, or acoustic vapor sensors. Sensors may include at least one sensor selected from the group consisting of surface acoustic wave sensors, shear horizontal wave sensors, flexural plate wave sensors, quartz microbalance sensors, conducting polymer sensors, dye-impregnated polymer film on fiber optic detectors, conductive composite sensors, chemiresistors, metal oxide gas sensors, electrochemical gas detectors, chemically sensitive field-effect transistors, and carbon black-polymer composite devices. The sensors are removable and/or replaceable.

A breath sample may comprise multiple breath compounds, including, but not limited to, alcohols, ethers, ketones, amines, aldehydes, carbonyls, carbanions, alkanes, alkenes, alkynes, aromatic hydrocarbons, polynuclear aromatics, biomolecules, sugars, isoprenes, isoprenoids, VOCs, VOAs, indoles, pyridines, fatty acids, and off-gases of a microorganism.

The present invention also provides a profile that may be generated from the sensor response, which may be used to prepare a diagnostic profile of a patient. Further, a diagnosis based on the profile may be produced using the diagnostic method.

In other embodiments, the present invention includes methods of collecting and analyzing a human breath sample, comprising: exhaling into a handheld sample collector; placing the handheld sample collector in fluid communication with a breath analyzer; transferring compounds from the sample collector into the breath analyzer for separation on a thermal desorption column; detecting compounds using two or more polymer-coated surface acoustic wave sensors; and wherein the handheld sample collector is not in fluid communication with the breath analyzer during the exhaling.

In other embodiments, the present invention includes an apparatus for collecting and detecting compounds in a human breath sample comprising: a handheld sample collector; a connector for connecting the handheld sample collector in fluid communication with a breath analyzer; a flow controller for transferring the breath compounds from the sample collector into the breath analyzer; and two or more sensors for detection of breath compounds.

The apparatus for collecting and detecting compounds in a human breath sample may be used to detect breath compounds for determining health or disease diagnosis, or for drug monitoring.

The handheld sample collector of the apparatus may collect breath compounds from multiple breaths. The handheld sample collector may comprise an exhaled breath collector containing a sorbent phase to absorb breath compounds from an exhaled breath. The sorbent phase may be selected from activated carbon, silica gel, activated alumina, molecular sieve carbon, molecular sieve zeolites, silicalite, $AlPO_4$, alumina, polystyrene, and combinations thereof. The handheld sample collector may further comprise an air collector, for compounds in environmental air, for collecting such compounds upon inhaling.

The breath analyzer system of the apparatus may comprise a thermal desorption column. In addition, the breath analyzer system of the apparatus may contain a mass spectroscopy, or electronic, optical, or acoustic vapor sensors. Electronic, optical, or acoustic vapor sensors may include at least one sensor selected from the group consisting of surface acoustic wave sensors, shear horizontal wave sensors, flexural plate wave sensors, quartz microbalance sensors, conducting polymer sensors, dye-impregnated polymer film on fiber optic detectors, conductive composite sensors, chemiresistors, metal oxide gas sensors, electrochemical gas detectors, chemically sensitive field-effect transistors, and carbon black-polymer composite devices.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 shows a top view of the breath sample collector with A) the related passages open upon inhalation, B) the related passages open upon initial exhalation, and C) the related passages open upon alveolar exhalation.

DETAILED DESCRIPTION OF THE INVENTION

The invention is directed to improved methods for collecting human breath samples and analyzing collected exhaled samples for compounds and devices described herein. The invention is also directed to the application of such methods in health or disease diagnosis, as well as therapeutic drug monitoring. The present invention utilizes the discovery that breath samples may be concentrated efficiently onto a stable adsorbent particulate phase with low back-pressure, thereby avoiding discomfort for the patient. In addition, the present invention utilizes efficient detection of the breath sample using multiple sensors simultaneously, reducing the run-time and accuracy significantly.

In one embodiment, a handheld two-sided sample collector (SC) is described which may be used to concentrate compounds from the exhaled breath on one side and from the air on the other side. The SC is then placed into a breath analyzer (BAS) system which pumps the concentrated breath sample through a thermal desorption column for separation. Compounds are desorbed from the column, which provides time resolution, and detected using electronic, optical, or acoustic vapor sensors. This combination of sample collection and analysis using portable, user-friendly devices provides an excellent alternative to conventional diagnostic techniques that are costly, time-consuming, and often unpredictable.

The invention includes several embodiments by which the SC and the BAS can be suitably modified for different applications or to offer sensitivity of each for different applications. The resulting sample collection and detection system may be used for detection for single breath compounds or multiple compounds for an overall diagnostic profile of a patient.

Thus, it is an object of the present invention to provide a method for collecting breath samples using a handheld sample collector with a sorbent phase to concentrate compounds from the exhaled breath.

It is a further object of the present invention to provide a method for collecting breath samples using a handheld sample collector with two sorbent phase compartments to concentrate compounds from the exhaled breath on one side and from the air on the other side.

It is a further object of the present invention to provide a method for collecting breath samples using a handheld sample collector that selectively samples the exhaled breath specifically from the alveolar space using flow divertor so that the first portion of the breath from the anatomical deadspace bypasses the sample collector.

In addition, it is an object of the present invention to provide such a handheld sample collector that controls sampling of the inhaled and exhaled breath when placed in contact with the mouth, thereby maximizing collection of compounds in the breath and environmental air. The subject may be any breathing animal, preferably a human patient, of interest.

It is another object of the present invention to provide such a handheld sample collector which is easy to use and which has either multiple breath sampling capabilities, or the ability to be conveniently reloaded.

It is still another object of the present invention to provide such a handheld sample collector that is mechanically simple, does not require depletable power sources, and which is relatively inexpensive.

The above and other objects of the invention are realized in specific illustrated embodiments of a handheld sample collector having a body with an inhalation passage and exhalation passages, which bypasses sampling the first portion of breath from the anatomical dead-space, and only collects breath from the alveolar space. The exhalation passage is formed by a first exhalation channel having a proximal end and a distal end, and a restricting flap or vane disposed near the distal end. The restricting vane is hinged within the primary exhalation passage to selectively inhibit the flow of air through the first exhalation channel. Thus, as the user exhales, forcing air from the proximal end to the distal end of the first exhalation channel, the hinged vane moves into a position to occlude a substantial portion of the channel, thereby limiting flow through the channel and subsequently into the exhaled breath collector.

It is a further object of the present invention to provide a method of analyzing the concentrated breath and air sample from the sample collector by using a portable breath analyzer system composed which thermally desorbs compounds from the sample collector using detection by either gas chromatography/mass spectroscopy, fiber-optic fluorescent sensors, or surface acoustic wave sensors.

In a variation of the above embodiment, the housing of the portable breath analyzer system includes a receptacle for the handheld sample collector, and the sensor module is removably mounted in the receptacle of the housing. In this embodiment, the sensor module can include one or more sensors.

Another specific embodiment of the invention provides a sensor module configured for use with a sensing apparatus. The sensor module is disposed within a housing that defines a receptacle. The sensor module includes a casing, an inlet and outlet connection for the handheld sample collector, a thermal desorption column, at least two sensors, and an electrical connector. The outlet port receives a test sample from the handheld sample collector and directs the test sample to the sample chamber. The sensors are located within or adjacent to the sample chamber and are configured to provide a distinct response when exposed to one or more analytes located within the handheld sample collector.

Methods for Collecting and Analyzing Human Breath

The method of the present invention generally involves collecting and analyzing human breath. Techniques for collecting and analyzing gas samples are well-known in the art, and include such methods as environmental gas sampling on sorbent tubes, as well as headspace and trap and purge sampling for gas chromatography and GC/MS analysis. General air sampling systems include smoke detectors, volatile chemical detectors, and infrared gas sensors specific to a particular compound (such as $CO_2$). In addition, detection of exhaled gases, such as oxygen, carbon dioxide, and nitric oxide, are typically used in hospitals and emergency rooms to report important patient conditions, as well as breath alcohol detectors in law enforcement. Specifically, though, detection of specific compounds in a breath sample requires reliable collection, processing, separation, and data interpretation to produce a reliable response.

Several vapor sensing technologies, including conducting polymers, electrochemical cells, gas chromatography/mass spectroscopy, infrared spectroscopy, ion mobility spectrometry, metal oxide semiconductor, photo-ionized detectors and surface acoustic wave sensors, have been evaluated for detection of compounds in the breath. Sensor sensitivity, selectivity, operating life, shelf-life, drift, linearity, initial cost, recurring costs, warm-up time, analysis time, power consumption, portability and calibration needs were evaluated. Although there is a large market opportunity to be able to diagnose medical conditions non-invasively by monitoring breath, one challenge is identifying the breath compounds, or analytes, that are present for each medical condition and determining if their concentrations are detectable. In addition, each person will have different concentrations and compositions of analytes (inter-patient variability), making analysis of diverse populations difficult. Typically, there will also exist chemically similar analytes that interfere with the analysis making selectivity of trace concentrations another important factor. Thus, a sensitive and specific sensor platform is needed that is portable and cost effective. The relevant gas sensor technologies are reviewed below (Table 1) comparing the selectivity, sensitivity to humidity, overall sensitivity, drift, size/portability, reproducibility on large scale, energy consumption, and initial and annual costs. The sensor systems reviewed include: gas chromatography (GC), mass spectroscopy (MS), Fourier-transform infrared spectroscopy (FTIR), metal-oxide sensor (MOS), photo-ionization detection (PID), conducting polymers/electrochemical (CP/EC), fiber-optic fluorescent sensor (FOFI), surface acoustic wave (SAW), and pre-concentrator/thermal-desorption surface acoustic wave (PC/TD SAW). In particular, the FOFI and PC/TD SAW sensors are discussed as particularly strong platforms, compared to GC/MS, for a sensitive commercial product.

TABLE 1

Comparison of different sensor platforms and requirements for a diagnostic system.

|  | GC/MS | FTIR | MOS | PID | CP/EC | FOFI | SAW | PC/TD SAW |
|---|---|---|---|---|---|---|---|---|
| Compound Selectivity | ++ | + | − | −− | − | + | − | ++ |
| Interferants/Humidity Sens. | ++ | + | − | − | −− | + | −− | ++ |
| Sensitivity | ++ | − | ++ | + | + | + | + | ++ |
| Drift | − |  | − | − | + | − |  | + |
| Size/Portable | −− | −− | + | + | + | ++ | ++ | ++ |
| Reproducibility/Mass Manufact. |  | − |  | + | − | ++ | + | ++ |
| Power/Energy Consumption | −− | −− | − | + | + | ++ | ++ | ++ |
| Initial Cost (<$1,000) | −− | −− | ++ | + | + | ++ | ++ | ++ |
| Annual Cost | −− | −− | ++ | − | − | ++ | ++ | ++ |

Gas Chromatography/Mass Spectroscory (GC/MS)

Gas chromatography/mass spectroscopy (GC/MS) is actually a combination of two technologies. One technology separates the chemical components (GC) while the other one detects them (MS). Technically, GC is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector, such as a Flame Ionization Detector (FID) or an Electrochemical Detector (ECD), converts the column eluent to an electrical signal that is measured and recorded. The signal is recorded as a peak in the chromatogram plot. Chromatograph peaks can be identified from their corresponding retention times. The retention time is measured from the time of sample injection to the time of the peak maximum, and is unaffected by the presence of other sample components. Retention times can range from seconds to hours, depending on the column selected the component, and the temperature gradient. The height of the peak relates to the concentration of a component in the sample mixture.

Mass spectroscopy is a detection method, which can be coupled with GC or sample directly from the headspace of a sample, which ionizes, fragments, and rearranges a molecule under a given set of conditions and makes identification of the molecular weight/charge (m/z) of molecules possible. A mass spectrum is a plot showing the mass/charge ratio versus abundance data for ions from the sample molecule and its fragments. The disadvantage of using MS independently from GC is that complex mixtures, such as breath, would provide an assembly of mass peaks that would be nearly impossible to interpret.

GC, and the combination of GC/MS, are the most accurate, selective, and sensitive sensor technologies. They are also the most complex systems to use, the most expensive ($50,000 for a base instrument), the least portable with the slowest analysis time (minutes to hours). Even with significant development efforts, the GC/MS system is not a feasible commercial breath detection system, although components of GC can be miniaturized with improved detector technologies.

Fiber-Optic Fluorescent Sensors (FOFI)

In a photoluminescent, or fluorescent, type optical sensor, a fluorescence molecule is immobilized in a polymer or sol-gel matrix, or onto a microsphere bead, and coated onto the end of optical fiber. The fluorescent compound, such as ruthenium (McEvoy, McDonagh et al. 1997), or dye, such as Nile Red (Albert, Walt et al. 2001), undergoes an intensity or wavelength shift upon changes in the microenvironment due to interactions with a volatile compound. The sensor response is provided by producing an excitation light pulse through an optic fiber and measuring the emission spectra the returns using a spectrometer. Some of the advantages of optical sensor over electrodes include reproducibility, small and light weight, large dynamic range, ease of multiplexing, ease of calibration, and low power (LED light source) requirement.

Surface Acoustic Wave (SAW) Sensors

Surface Acoustic Wave (SAW) sensors are constructed with interdigital metal electrodes fabricated on piezoelectric substrates both to generate and to detect surface acoustic waves. Surface acoustic waves are waves that have their maximum amplitude at the surface and whose energy is nearly all contained within 15 to 20 wavelengths of the surface. Because the amplitude is a maximum at the surface such devices are very surface sensitive. Because of the popularity of cell phones, SAW devices, which act as electronic bandpass filters in hermetically sealed enclosures, have the highest sensor-to-sensor signal reproducibility of any of the systems described. In addition, they are small, require low-power, and are low-cost.

SAW chemical sensors take advantage of this surface sensitivity to function as sensors. If a SAW device is coated with a thin polymer film it will affect the frequency and insertion loss of the device. If the device, with the chemo-selective polymer coating, is then subjected to chemical vapors that absorb onto the surface, then the frequency and insertion loss of the device will further change. It is this final change from baseline that allows the device to function as a chemical sensor.

If several SAW devices are each coated with a different polymer material through spray-coat or spin-coat techniques, the response to a given chemical vapor will vary substantially from device to device based on the thickness and morphology of the final film, but alternative techniques of producing reproducible coatings are also available. The polymer is normally chosen so that each will have a different chemical affinity for a variety of organic chemical classes, i.e., hydrocarbon, alcohol, ketone, oxygenated, chlorinated, and nitrogenated. If the polymer films are properly chosen, each chemical vapor of interest will have a unique overall effect on the set of devices. SAW chemical sensors are useful in the range of organic compounds from hexane on the light, volatile extreme to semi-volatile compounds on the heavy, low volatility extreme.

Breath Sample Collector (SC)

In general, the breath sample must be concentrated onto a sorbent trap over several breaths to extract low concentration compounds-of-interest. It is desirable that a sample collector (SC) be portable, preferably a small handheld device similar to an asthma drug inhaler, that may be used to collect breath samples from patients and then processed on a central detection system that is also portable and user-friendly. It is also desirable that the SC collect several breaths from the alveoli of the lungs, which contain the volatile compounds of interest present in the lung or have diffused from the blood. Air from the 'anatomical dead-space' originating from the pharynx, trachea, and bronchial tree where no gaseous interchange occurs should not be sampled. Finally, since the content of the environmental air may contain low concentrations of the compounds of interest, it would also be desirable that a sample of the air that is inhaled be collected onto a sorbent trap in a similar manner for comparison.

A SC with a sorbent tube which a patient exhales directly through has been shown to produce excellent absorption and desorption properties using common sorbent phase used in GC. The sorbent tube, typically approximately ¼ inch in diameter and 4 to 10 inches in length, produces low back-pressure from coarse particulates with minimal moisture absorption and high collection efficiency. The SC may also use an exhalation cavity, which is designed with one-way flaps to only capture certain portions of the exhaled breath, to obtain optimum sampling over multiple breaths. The SC is ideally fashioned with two sorbent tubes for collection of air upon inhalation and breath compounds upon inhalation, and can be used to flow the inhaled and exhaled gases simultaneously or in two separate sampling phases. The SC can be made of plastic, low weight and low cost, and may be used in a remote location and attached to the breath analyzer later for processing.

Breath Analyzer System (BAs)

The gas sample that is introduced into the sensor system, using a headspace analyzer or a sorbent column, needs to be delivered without loss of signal by absorption to tubing and connections. The flow rate of the gas sample is regulated to control sampling variability, similar to GC, using a regulated gas supply. Interaction between the captured gas sample and gas flow system components, such as valves, pumps, and tubes, are minimized in the system design, i.e. non-adsorbing tubing, valves, etc. We recently observed in an animal study significant losses of an exhaled medication were detected from adsorption to certain types of porous tubing (unpublished results). For a 4-SAW BAS system, a mini-GC column is used to capture and separate compounds at 100–400 ml/min to optimize absorption onto the thermal desorption column. Furthermore, the temperature gradient is ramped from 60° C. to 240° C. over 40–80 seconds to desorb compounds for detection on, for example, a 4-SAW array. Optimization of these conditions for each sample is performed using a mathematical model to systematically investigate the effects of column packing, column temperature gradient, and gas flow to produce optimized sampling and analysis systems for a variety of diagnostic profiles.

A miniature gas chromatography (GC) column, or thermal desorption (TD) column, is used to capture vapors of interest from the SC and obtain time resolution detection. Molecules are absorbed onto the packed TD column as the gas sample flows through it and desorb in a temperature-dependant manner proportional to the vapor pressure of an analyte. Different molecules desorb at different temperatures, similar to GC, so time resolution of different compounds, proportional to the temperature gradient, is obtained. Time and the increase in column temperature yields a time resolution between the desorption of different molecules, as well as differences in the response of the 4 different sensors, resulting in a chromatogram for each sensor. The resulting data output is enhanced using the selectivity to the 4 different polymer-coated sensors and allows for recognition between multiple compounds in the breath or the presence of interferants (such as coffee or tobacco). In general, the packing material in the TD column, sampling time, temperature range, and entire gas-flow system will be optimized for the analytes of interest, as well as for separation from interferring species.

An example of the BAS is composed of 3 electronic subsystems include the following modules: (1) SAW oscillation circuits, (2) frequency counters, and (3) the controlling unit. The SAW oscillation circuits are responsible for generating a baseline resonant frequency based on the particular polymer coating applied to the SAW and a shifted resonant frequency based on the adsorption of the sample vapor to the individual polymer coated SAWs within the sensor array. The frequency counter determines the resonant frequency of the SAW resonator circuits and converts it to a voltage for analysis. The control module is responsible for sampling and conditioning input signals as well as multiplexing and timing communication with external devices.

One configuration to measure SAW responses is to measure the frequency shifts based on a SAW resonator configuration. This delay line resonator configuration not only requires less circuitry but also gives responses with vastly superior precision than the pure delay line circuit, which measures amplitude variations compared to an external input signal. The resonator circuit is simply composed of the SAW sensor and a class A feedback amplifier with a gain greater than the signal attenuation that occurs in the SAW delay line, the SAW interdigital transducer electrodes (IDT), and supporting circuitry. The resonant frequency of the circuit is primarily determined by the SAW delay line characteristics such as delay line length and substrate material and IDT characteristics including finger amount and spacing. Sensitivity has been shown to be proportional to resonant frequency, however noise also increases with frequency. Previous studies with SAW devices in the hundreds of megahertz range have shown sensitivities into the ppb (parts per billion) range with comparable sensitivities to GC.

The frequency counter outputs an analog voltage of the form $v(t)=G(t)f(t)$ where $v(t)$ is a real time voltage, $f(t)$ is the resonant frequency, and $G(t)$ is a device dependent function. The frequency counter is multiplexed between the different sensors based upon the particular integrated circuit or device that is used. This analog output is then converted to digital data via an A/D converter normally on most common digital signal processor (DSP) or microcontroller chips. The controlling unit is composed of common DSP and/or microcontrollers, which provide extremely precise timing abilities as well as on-board AND conversion mechanisms, standard communication interfaces such as RS-232, and I/O ports for control mechanisms and memory interfacing.

Feature extraction is the task of extracting relevant signal parameters, such as retention time through the thermal desorption column or sensor response ratios, from raw sensor signals. Standard measurements are made relative to a clean reference headspace sample, such as 1-bromo4-fluoro-benzene. A typical measurement consists of exposing the sensor array to a reference, providing a baseline value, and comparing the reference to sample runs or adding the reference to the sample at a known concentration, referred to as an internal standard. Similar to a GC sample run, a compound is introduced onto the column and then a valve switches allowing flow of the carrier gas, in this case air, across the sensors. As the thermal desorption column ramps to higher temperatures the various vapors are desorbed and exposed to the sensors for a given time (based on the association/dissociation of the vapor for the given polymer coating), which causes a change in the output/frequency of the 4 different sensors. Retention/desorption times and sensor responses may be referenced according to the internal standard to better test the model. The sensor response may span several seconds where the vapor desorbs from the column and the sensors have a rise time where the vapor associates with each sensor to a maximum and a decay time to return to the baseline value. From the response curve for each sensor features are extracted. The most common parameters extracted are the retention time of the peak and the individual sensor responses or ratios from a baseline level.

Apparatus for Collecting and Analyzing Human Breath

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1A:
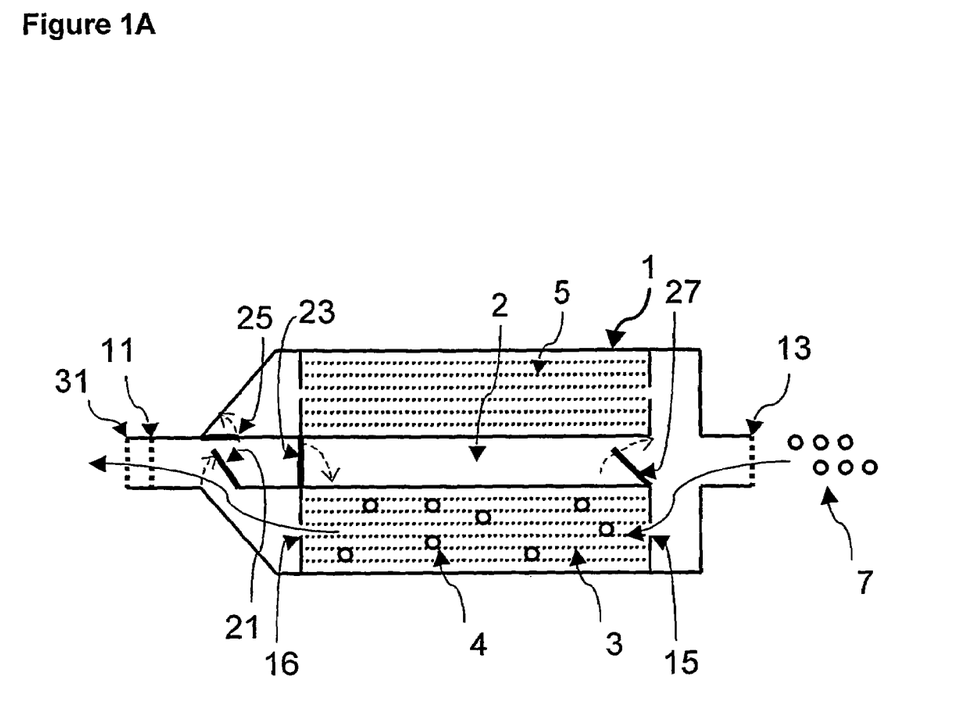
Figure 1B:
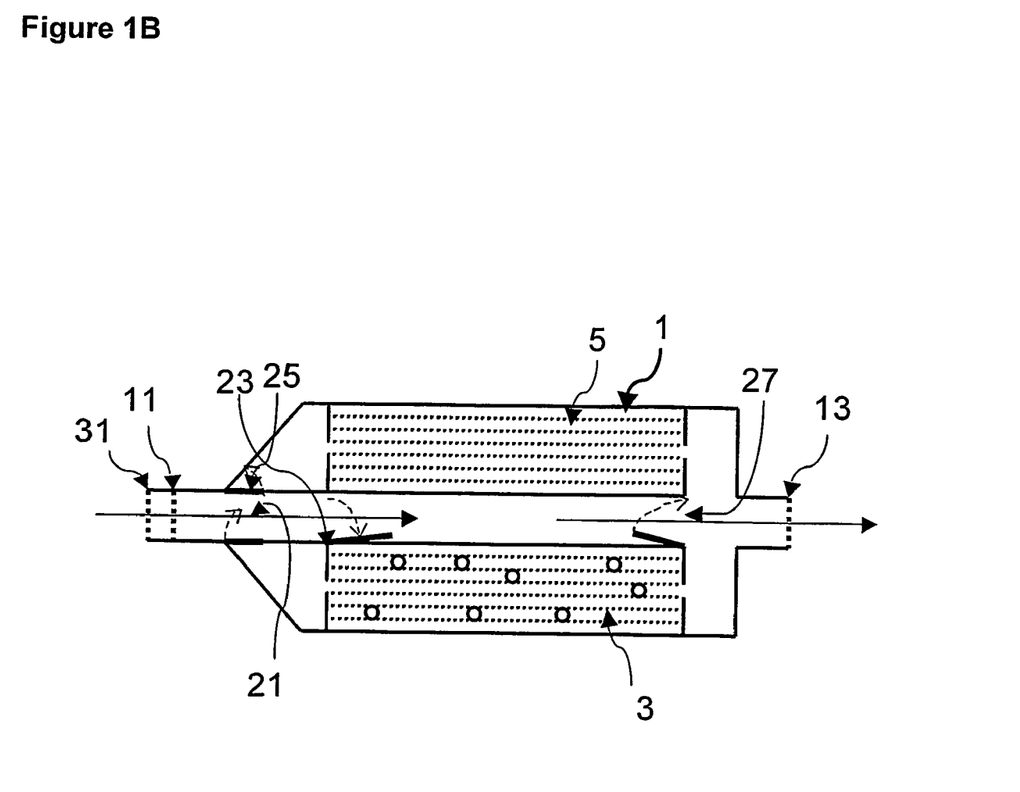
Figure 1C:
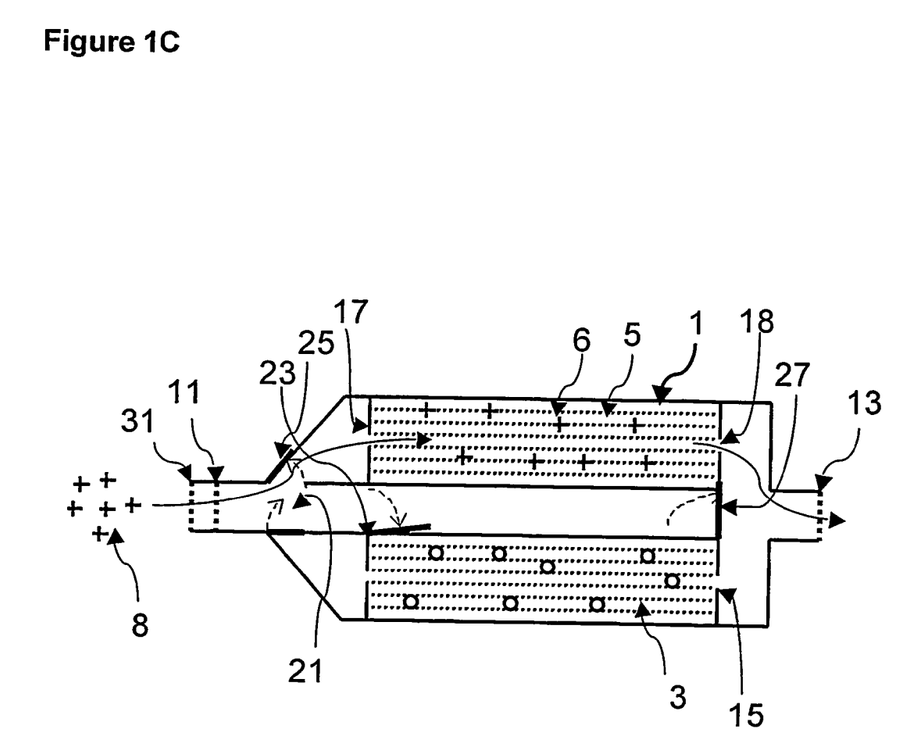
Figure 2:
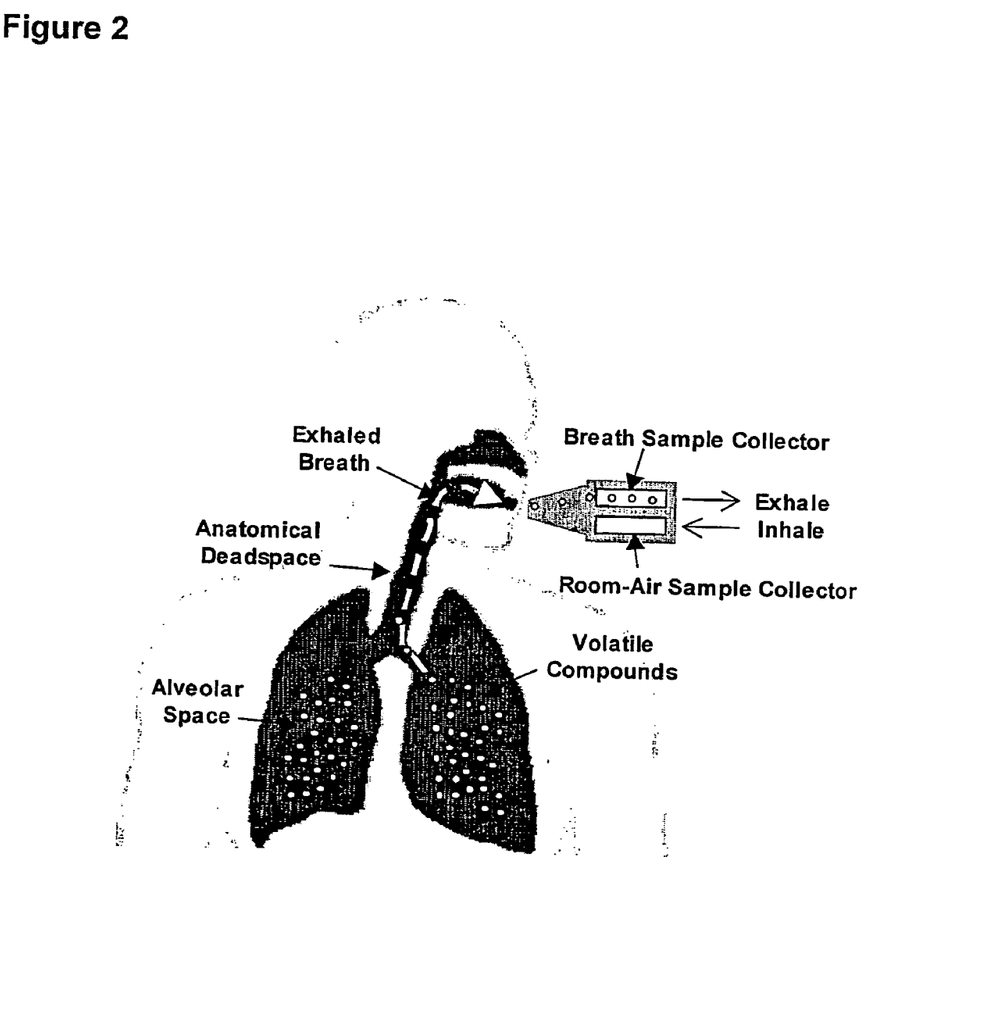
FIG. 2 is an anatomical illustration depicting the human respiratory system and collection of alveolar breath into the sample collector.

The general design of the breath sample collection (SC) device is shown in FIG. 1A to 1C and an anatomical description of a human exhaling through the breath sample collector in FIG. 2. The apparatus shown in FIG. 1A to 1C of the main housing 1 of the handheld sample collector with outside air collector 3 and a exhaled breath collector 5. The mouth is placed in contact with the mouthpiece tube 11 that is an oriface with a grating that restricts flow to improve sample collection. Inserted on the mouthpiece an optional disposible cylinder 31 with a filter for reusing the SC without contamination is provided.

FIG. 1A depicts the air-flow through the air collector 3 and collection of concentrations of environmental volatile compounds 7 upon inhalation. Upon inhalation air is drawn through the mouthpiece orifice 11 which opens a vane 21 while vane 23 and 25 remain closed. Air is drawn through the rear orifice 13 and through air collector opening 15 and through the stationary collector phase. Environmental volatile compounds 7 are collected onto the stationary collector phase (shown as 4) and air exits air collector opening 16, through vane 21, and inhaled through mouthpiece orifice 11.

FIG. 1B depicts the initial air-flow through the bypass exhalation cavity 2 for avoiding collection of dead-space air upon exhalation. Upon the initial exhalation, breath flows through the mouthpiece orifice 11 which closes vane 21 and opens vane 23 and 25. The stationary collector phase of exhaled breath collector 5 restricts initial flow upon exhalation and the breath passes through the bypass exhalation passage 2. Vane 27, which is designed to close at an assigned flow in conjunction with the mouthpiece oriface 11, is initially open allowing the first portion of the exhaled breath to flow out rear oriface 13. After the initial portion of the exhaled breath bypasses the exhaled breath collector 5, vane 27 closes and the exhaled breath is diverted through vane 25.

FIG. 1C depicts the collection of volatile compounds of interest in the exhaled breath through the exhaled breath collector 5. After vane 27 closes, the exhaled breath is diverted through vane 25 and through exhaled breath collector opening 17 and through the stationary collector phase of the exhaled breath collector 5. Exhaled volatile compounds 8 are collected onto the stationary collector phase (shown as 6) and breath exits through opening 18 and out rear orifice 13.

Suitable commercially available adsorbent materials for the collectors have been investigated (Groves, Zellers et al. 1998) and include, but are not limited to, activated carbon, silica gel, activated alumina, molecular sieve carbon, molecular sieve zeolites, silicalite, $AlPO_4$, alumina, polystyrene, TENAX series, CARBOTRAP series, CARBOPACK series, CARBOXEN series, CARBOSEIVE series, PORAPAK series, SPHEROCARB series, Dow XUS series, and combinations thereof. Preferred low-pressure adsorbent combinations include, but are not limited to, TENAX TA and GR, CARBOTRAP, and Dow XUS565. Those skilled in the art will know of other suitable absorbent materials.

An anatomical description of a human exhaling through the breath sample collector is shown in FIG. 2. As shown, the breath sample of interest for testing from the alveolar space can be separated from the dead-space air in the breath, which typically is the first 100–300 ml of the exhaled breath. For collecting the highest concentration of volatile compounds of interest present in the breath, several collection factors must be optimized including the full expiratory volume (FEV) and expiratory flow (EF) of the patient, the portion of exhaled breath sampled, type and amount of stationary phase, and the number of breaths collected. Through the optimized design of the SC, (A) the full expiratory volume (FEV) and the portion of exhaled breath sampled may be optimized to fit the general population, (B) the expiratory flow may be restricted through mouthpiece orifice and the type and density of the stationary phases, (C) the number of breaths can be controlled by inserting an optional counter that signals the user that the sampling is complete or bypasses all further exhaled breaths to flow through the bypass tube 2 shown in FIG. 1. In addition, it may be of interest to sample the air and the exhaled breath in separate breaths through modification of the SC so the alveolar gradient of exhaled volatile compounds is not reduced through collection after passing through the air collector.

Figure 3:
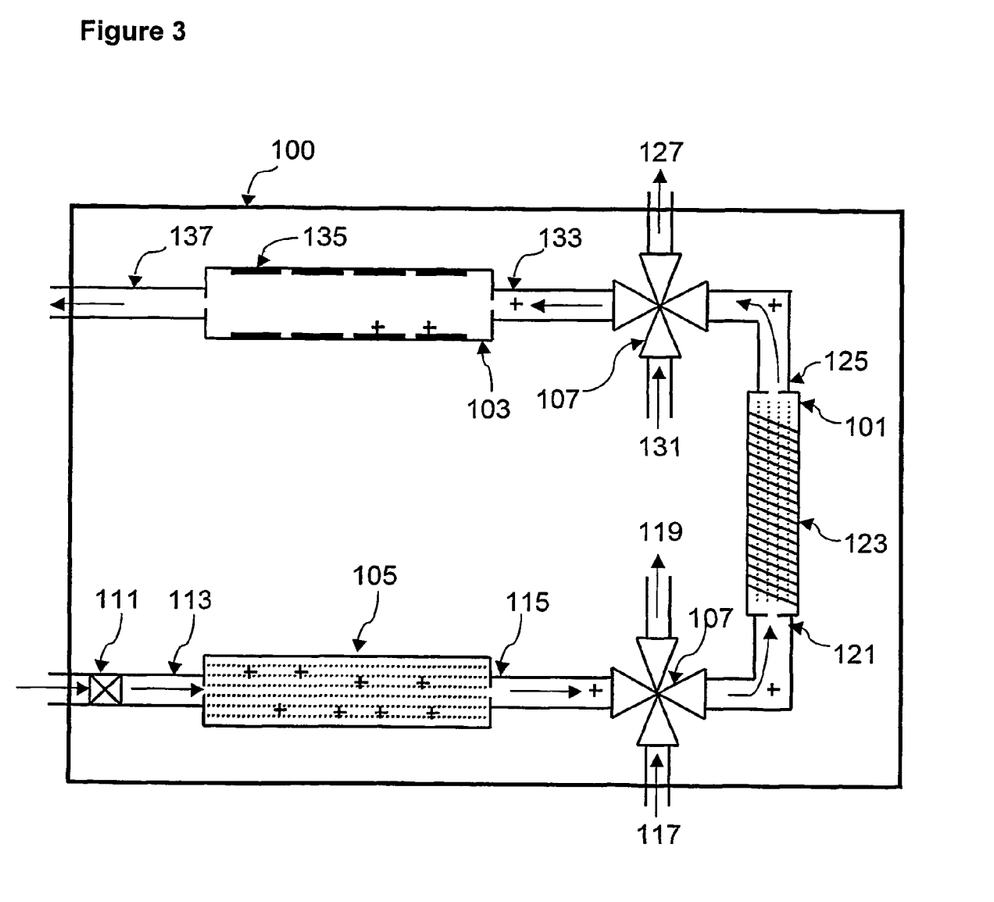
FIG. 3 is a general illustration of the design of the breath analyzer system.

The general apparatus shown in FIG. 3 of the breath analyzer system (BAS) 100 may be used to analyze the air and exhaled breath samples collected with the SA shown FIGS. 1A to 1C. This design, utilizing a (1) method of connecting the SC 105 to transfer volatile compounds to the (2) thermal desorption column 101 for further separation and then detection in the (3) sensor module 103, offers several advantages including portability, sensitivity, and reproducibility not previously investigated. While previously described systems utilize less-sensitive online breath detection methods (RYBAK, THEKKADATH et al. 1999; Sunshine, Steinthal et al. 2001) and more cumbersome breath sampling techniques (Phillips 1995; Lewis, Severin et al. 2001) or collection bags (Kubo, Morisawa et al. 1999), the described technique takes advantage of highly efficient collection of compounds in the breath and detection using a highly sensitive portable detection system.

As depicted in FIG. 3, the breath analyzer system (BAS) 100 is generally similar to a GC with motors, pumps, and valves required to bring the sample from the SC 105 into the thermal desorption column 101 for separation and then detection in the sensor module 103. In the sample LOAD phase, dry-air or an inert gas 111, which is temperature and humidity controlled, enters the SC 105 through connection 113. Volatile compounds move out the SC 105 through connection 115 and through valve 107 to the thermal desorption column 101. In a preliminary step a dry-air purge that bypasses the thermal desorption column 101 may be performed by opening valve 119. The gas sample enters the thermal desorption column 101 through connection 121 which then absorbs to the stationary phase in a similar manner to sample collection. Gas flow in this phase may be directed over the sensor module 103 or bypassed through valve 127. The temperature of the thermal desorption column 101, controlled by a series of NiCr windings 123 around the column or other suitable heating setup, in this phase is generally below 100° C. for collection of most compounds on the stationary phase.

During the RUN phase, dry-air or an inert gas sample enters valve 117, bypassing the SC 105, and the thermal desorption column 101 is heated to release the compounds for detection through valve 107, connection 133, and into the sensor module 103 and out passage 137, over a much shorter time span than generally used for GC. The sensors 135 arrayed in a series of 2 to more than 32 in the sensor module 103, are monitored for electrical, acoustic, or optical changes relative to time during the run. Since the sensors 135 are designed to have chemoselectivity to different classes of compounds, selectivity of compounds may be performed through time resolution and sensor response. During the PURGE phase, dry air may be used to purge the thermal desorption column 101 entering through valve 117 as well as the sensor module 103 entering through valve 131.

Example sensors for detection in the sensor module include, but are not limited to, polymer-coated SAW sensors and fiber-optic fluorescence sensors. SAW sensors are reasonably priced (less than $200) and have good sensitivity (tens of ppm) with very good selectivity. They are portable, robust and consume nominal power. They warm up in less than two minutes and require less than one minute for most analysis, and require no calibration. SAW sensors do not drift over time, have a long operating life (greater than five years) and have no known shelf life issues. They are sensitive to moisture, but this is eliminated with the use of the dry-air purge and thermal-desorption column. Fiber-optic fluorescent sensors also have similar properties to SAW sensors in general, but also are disposable since only the tip of the probe is replaced and no electronics like the SAW sensors. On board microprocessor electronics is required to control the sequences of the system and provide the computational power to interpret and analyze data from the array. An advantage of this technique, though, is that improved sensitivity through control of analyte desorption and gas flow, as well as direct comparison and validation using GC, is possible.

Exhaled Markers of Disease ad Oxidative Stress

The analysis of exhaled breath provides an excellent means of assessing VOC's present in the body from a variety of conditions. The rapid equilibration between concentrations in the pulmonary blood supply and in alveolar air is known. The diagnostic potential of breath analysis has been recognized for many years, and links have been established between specific volatile organic vapor metabolites in the breath and several medical conditions (Manolis 1983). In 1971, Pauling found that normal human breath contained several hundred different VOCs in low concentrations (Pauling, Robinson et al. 1971). Since then, more than a thousand different VOCs have been observed employing progressively more sophisticated and sensitive assays in low concentrations in normal human breath (Phillips 1997).

In general, normal human alveolar breath contains a large number of volatile organic compounds in low concentrations (nanomolar or picomolar) present from local and systemic cellular biological processing and metabolism. Therefore, the analysis of breath offers an excellent platform for the monitoring of various biological states. Another application is the evaluation of exposures to industrial solvents such as benzene, toluene, styrene (Droz and Guillemin 1986). The non-invasive nature of monitoring exposure of these volitile compounds by sampling the breath makes it potentially more rapid and convenient than blood or urine analysis. However, high background concentrations of water vapor and the presence of certain endogenous organic vapors make the collection of accurate measurements more difficult using standard techniques (Groves and Zellers 1996).

Volatile organic compounds (VOCs) may be absorbed and/or metabolized from the inspired air (negative gradient) or added to alveolar breath as products of metabolism (positive gradient). Some features of this transformation have been well understood for many years: e.g., acetone exhaled in diabetic patients (Manolis 1983) and increased carbon dioxide by metabolism of glucose (Phillips 1992). In addition, there is evidence alveolar breath may be used to diagnose several other disorders including lung cancer, liver disease, inflammatory bowel disease, rheumatoid arthritis and schizophrenia (Phillips, Erickson et al. 1995; Phillips, Gleeson et al. 1999; Phillips, Cataneo et al. 2000). Thus, the chemical analysis of breath therefore provides a non-invasive diagnostic test for the diagnosis of these and other diseases.

Volatile Compounds from Bacterial Infection

The 13C-urea breath test is a well known accurate, noninvasive diagnosis of active *Helicobacterpylori* infection and can document post-therapy cure (Opekun, Abdalla et al. 2002). Results of several studies have shown that *Pseudomonas, Klebsiella pneaumoniae, Proteus mirabolis, Staphylococcus aureus, Enterococcus, Clostrdium, E. coli*, and *M. tuberculosis* emit volatile compounds into the headspace of cultures (Larsson, Mardh et al. 1978; Labows, McGinley et al. 1980; Pons, Rimbault et al. 1985; Rimbault, Niel et al. 1986; Zechman, Aldinger et al. 1986; Cundy, Willard et al. 1991; Jenkins, Morris et al. 2000; Yu, Hamilton-Kemp et al. 2000; Aathithan, Plant et al. 2001). The volatile profiles of cultures of several bacterial strains reveal various acids, alcohols, aldehydes, ketones, and amines using gas chromatography (GC). While direct sampling of the bacteria culture media and swab culture samples from patients mouths provide more direct ways to detect strain and concentration, breath sampling offers many advantages including speed and reproducibility.

First, different strains of bacteria, such as *E. coli* and *Clostridium*, are so different biochemically that they emit very characteristic compounds, which provide a fingerprint for each genus and species. Using GC techniques, chemical groups or specific compounds have been identified as typical volatile metabolites for certain bacteria (Labows, McGinley et al. 1980; Cundy, Willard et al. 1991). For example, *Pseudomonas aeruginosa* produced a characteristic profile of methyl ketones (excluding 2-tridecanone) and 1-undecene as a major component; however, no indole was found in this organism (Zechman and Labows 1985; Zechman, Aldinger et al. 1986). Recently, as part of the development of digital aroma technology, studied headspace compounds from several bacteria including *P. aeruginosa* and *E. coli*, alcohols including ethanol were identified as the primary products isolated (Arnold and Senter 1998). Second, sampling of the breath offers a non-invasive sampling route for identification of specific compounds for detection of bacteria and other organisms, especially for infection in the throat and lungs.

A rapid, non-invasive, and easy-to-use diagnostic system for detection of tuberculosis (TB), for example, using a patient's breath could substantially improve global control strategies. Although progress over the last decade has improved the speed and quality of TB diagnostic systems in industrialized countries, a cost effective system for use in third-world countries where TB is prevalent is still not available. The composition and concentration of volatile compounds emitted from TB-infected cells in the lung is largely unknown. However, detection of tuberculostearic acid (TSA) in TB cultures and sputum and serum samples of TB patients using gas chromatography/mass spectrometry (GC/MS) methods suggests the presence of characteristic metabolites that might be useful in diagnosing TB. While direct sampling of a large volume of exhaled breath of infected patients could be sampled using Tedlar bags and analyzed with methods such as GC/MS, low bacillary load, patient-to-patient variability, as well as intra-day to inter-day sampling, would most likely not lead to a strong signal to identify a characteristic profile. Unfortunately, similar to the other exhaled compounds reviewed for detection, there is the concern that dilution with dead-space air and that the lung and throat tissue may absorb and metabolize a fraction of the emitted volatile compounds. Thus, a breath analysis system with very low limits of detection (LOD) is described to help rapidly diagnose patients in the active disease stage, as well as test response to anti-tuberculosis therapies and vaccines pre and post-exposure.

Drug Monitoring

The degree of effects from an administered drug, as well as the side effects, is directly related to absorption, distribution, metabolism, and elimination (ADME) of the drug at the site-of-action. The concentration at the site-of-action determines the therapeutic effects, which for most drugs is related to the systemic levels of the drug in the blood after oral, injected, inhaled, or administered through other forms of drug delivery. Therefore, the "drug" will be taken to be any chemical agent that is administered to provide therapeutic effects, or alternatively administered as a diagnostic aid.

Although drugs are administered to provide beneficial therapeutic effect, often drugs can also cause mild to severe side effects, which are directly related to the concentration of the drug in the body. The concentration of the drug in the body, in turn, is regulated both by the amount of drug ingested by the subject over a given time period, or the dosing regimen, and the rate at which the drug is eliminated from the body. Therapeutic drug monitoring for improving therapies normally requires the collection and analysis of a blood sample. Such tests are invasive, complex, and require extended time for analysis. While most drugs are eliminated renally or hepatically, many drugs and metabolites are also eliminated through the breath by crossing the liquid: gas barrier in the lung. Although different levels of a drug would be present in the exhaled breath depending on partitioning, breath rate, and physical state of the person and lungs, after factoring losses for collection and detection variations in the detected breath concentration versus time should be proportional to the systemic concentrations. This invention provides an excellent, non-invasive means of providing information on the systemic drug profile for tailoring drug dose or dosing regimens. Examples of "narrow therapeutic window" drugs or drugs with harmful side effects for which therapeutic drug monitoring is used include bupivacaine, coumadin, cyclosporine, insulin, and anesthetic agents such as propofol. In addition, exhaled metabolites or markers of side effects may also be monitored using the described system, as well as simply detecting the presence of a drug or marker to monitor patient compliance to drug regimens. The erythromycin and 13C-urea *H. pylori* breath tests are such examples where specific metabolic pathways lead to exhaled products which may provide important markers (Lee, Gwee et al. 1998; Rivory, Slaviero et al. 2001). Monitoring of drug levels or flavoring agents may also be performed to monitor adherence to drug regimens after dosing to improve patient outcomes.

EXAMPLES

The following examples are included to demonstrate example embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention.

Example 1

Menthol Detection

Analysis of a gas sample of menthol was produced in accordance with the present invention. Menthol is a common agent in chewing gum and cigarettes. A sample of menthol crystals (200 mg, Spectrum Chemical) was placed into a 20 ml glass vial placed into a water bath at 37° C. Breathing was simulated using a Pulmosim (Blease) set for 1000 ml breaths and a one-way valve connected at the output to produce an exhaled breath every 10 seconds. The vial was connected to the bottom of a ½" T-connection and allowed flow to travel over the headspace of the menthol, liquid at 37° C. A stopper was fixed to the other side of the T-connector and a 1 liter Tedlar bag (1 breath) and sorbent tubes (12 inches long, ¼" diameter) with 2 g of Tenax GC (20/35, Alltech) and Carbotrap (20/40, Supelco) were connected for sampling.

The detection system currently utilizes a PC/TD 4-SAW setup as shown in FIG. 3. Three of the four SAW sensors were coated with ethyl-cellulose (A), polyisobutylene (B), and polyepichlorohydrin (C) with acceptable thicknesses (10–50 nm) while one remained uncoated as a control (D). The SAW resonator frequencies were simultaneously monitored after desorption from the thermal desorption column producing 4 individual profiles with time of menthol. The thermal desorption/pre-concentrator column (1 inch long, $\frac{1}{16}$" diameter) was packed with Tenax GC packing and a 40 second flow was used (at 130 ml/min) for the LOAD phase and an 80 second flow (at 400 ml/min) was used for the RUN phase with a thermal ramp of 2° C./second. The sensor response from the Tedlar bag sample showed two peaks at 15 and 25 seconds with a sensor affinity of D>C>B>A, and similar (but lower) sensor responses following desorption from Tenax and Carbotrap after desorption at 70–80° C. In this fashion, breath samples could be collected following oral dosing of a menthol-containing formulation (i.e., a tablet or inhaler), or other flavoring agents, and communicated to a doctor or pharmacist to confirm that a patient is adhering to a drug regimen at home.

Example 2

Pentane Detection

Analysis of a gas sample of pentane was produced similar to Example 1 in accordance with the present invention. Polyunsaturated fatty acids are found in the cellular and subcellular membranes and are prone to lipid peroxidation as a result of the extremely weak binding of the hydrogen atoms to the carbon chain. Increased breath alkanes, particularly ethane and pentane, have demonstrated increased oxidative stress in breast cancer, rheumatoid arthritis, heart transplant rejection, acute myocardial infarction, schizophrenia, and bronchial asthma (Phillips 1992). A sample of n-pentane (1 ml, Fisher, HPLC grade) was similarly placed into a 20 ml glass vial placed into a water bath at 37° C. Samples were collected in a Tedlar bag and onto Tenax GC and Carbotrap sorbent tubes and analyzed using the 4-SAW sensor array. The SAW resonator frequencies were simultaneously monitored after desorption from the thermal desorption column again producing 4 individual profiles with time of pentane. The sensor response from the Tedlar bag and the sorbent tubes showed a single peak at 42 seconds with a sensor affinity of A>C>B=D, and similar (but lower) sensor responses following desorption from Tenax and Carbotrap after desorption at 70–80° C. In this fashion, breath samples may be analyzed for detection/diagnosis of various disease of oxidative stress.

Example 3

Ethanol Detection

Analysis of a gas sample of ethanol production from *E. coli* culture was produced similar to Example 1 in accordance with the present invention. Ethanol has been previously observed in *E. coli* fermentation, as well as *Clostridium*, using headspace sampling and GC analysis. One milliliter samples of ethanol, 1-isopropanol (internal standard), and acetic acid standards, as well as *E. coli* culture, were similarly placed into a 20 ml glass vial placed into a water bath at 37° C. Direct headspace sampling, as well as samples collected in a Tedlar bag and onto Tenax GC and Carbotrap sorbent tubes similar to Example 1, were analyzed using the 4-SAW sensor array. GC chromatograms with 1-propanol internal standard were also identified using a Varian 3600 GC with an HP 19395A of Lowry broth and *E. coli* showed peaks corresponding to ethanol, which is produced by *E. coli* during the fermentation process, 1-propanol, and acetic acid, which is a component of Lowry broth, at 2.3, 2.8, and 6.5 minutes, respectively, on a fused silica column with a temperature ramp of 20 degrees/minute. The 4-SAW sensor responses and time resolution for ethanol, 1-propanol, and acetic acid standards, as well as *E. coli* culture, showed varying sensor responses to the polymer coated SAWs for each low molecular weight compound. The compounds were desorbed quickly into the sensor array, with resolution times of 8, 20, and 4 seconds for ethanol, 1-propanol, and acetic acid, respectively. Using control of the pre-concentrator thermal profile a stable baseline, short retention times, and affinity for water can be controlled. Also, Tenax-GC thermal desorption column phase is selective for high boiling compounds such as alcohols, phenols, and monoamines, but other packings such as Carbowax, Porapak, and Chromosorb (Alltech) may be used depending on separation of the desired compounds. In this fashion, breath samples may be analyzed for detection/diagnosis of various bacterial infections from emitted gases, or indirectly from emitted gases such as ammonia from metabolism of urease activity of *H. pylori* after ingestion of urea. In addition, sampling and storage of breath samples onto sorbent tubes for alcohol level determination by law enforcement may be performed more accurately than before using the described invention.

Example 4

Propofol Detection

Analysis of a gas sample of propofol was produced similar to Example 1 in accordance with the present invention. Propofol is an anesthetic agent that is infused during surgery and subject to high patient-to-patient variability in distribution and clearance (Favetta, Degoute et al. 2002). Current multi-gas anesthesia monitors (SAM® Monitor, GE Medical Systems), as well as vital sign monitoring, provide less sensitive and incomplete monitoring during surgery and deaths from over-anesthetizing patients has been reported (Sear and Higham 2002). A sample of propofol (1 ml, Sigma) was similarly placed into a 20 ml glass vial placed into a water bath at 37° C. Samples were collected in a Tedlar bag and onto Tenax GC and Carbotrap sorbent tubes and analyzed using the 4-SAW sensor array. The SAW resonator frequencies were simultaneously monitored after desorption from the thermal desorption column again producing 4 individual profiles with time of propofol. The sensor response from the Tedlar bag was not present, but sensor responses direct headspace sampling and from the sorbent tubes showed two peaks at 15 and 35 seconds with a sensor affinity of D>A>C>B. In this fashion, drug levels may be analyzed from sampling a patients breath during anesthesia for monitoring. In addition, other drugs may be detected directly or metabolic products, such as in $14CO_2$ with erythromycin, from analysis of the exhaled breath.

CITED DOCUMENTS

The following literature citations as well as those cited above are incorporated in pertinent part by reference herein for the reasons cited in the above text:

Aathithan, S., J. C. Plant, et al. (2001). "Diagnosis of Bacteriuria by Detection of Volatile Organic Compounds in Urine Using an Automated Headspace Analyzer with Multiple Conducting Polymer Sensors." *J Clin Microbiol* 39(7): 2590–3.

Albert, K. J., D. R. Walt, et al. (2001). "Optical multibead arrays for simple and complex odor discrimination." *Anal Chem* 73(11): 2501–8.

Arnold, J. and S. Senter (1998). "Use of digital aroma technology and SPME to compare volatile compounds produced by bacteria isolated from processed poultry." *J. Sci. Food Agric* 78: 343–348.

Cundy, K. V., K. E. Willard, et al. (1991). "Comparison of traditional gas chromatography (GC), headspace GC, and the microbial identification library GC system for the identification of Clostridium difficile." *J Clin Microbiol* 29(2): 260–3.

Droz, P. O. and M. P. Guillemin (1986). "Occupational exposure monitoring using breath analysis." *J Occup Med* 28(8): 593–602.

Favetta, P., C. S. Degoute, et al. (2002). "Propofol metabolites in man following propofol induction and maintenance." *Br J Anaesth* 88(5): 653–8.

Groves, W., E. Zellers, et al. (1998). "Analyzing organic vapors in exhaled breath using a surface acoustic wave sensor array with preconcentrator: Selection and characterization of the preconcentrator adsorbent." *Anal Chim Acta* 371: 131–143.

Groves, W. A. and E. T. Zellers (1996). "Investigation of organic vapor losses to condensed water vapor in Tedlar bags used for exhaled-breath sampling." *Am Ind Hyg Assoc J* 57(3): 257–63.

Jenkins, R. O., T. A. Morris, et al. (2000). "Phosphine generation by mixed-and monoseptic-cultures of anaerobic bacteria." *Sci Total Environ* 250(1–3): 73–81.

Kubo, Y., K. Morisawa, et al. (1999). Apparatus and breathing bag for spectrometrically measuring isotopic gas. USPTO. US, Otsuka Pharmaceutical Co., Ltd.

Labows, J. N., K. J. McGinley, et al. (1980). "Headspace analysis of volatile metabolites of Pseudomonas aeruginosa and related species by gas chromatography-mass spectrometry." *J Clin Microbiol* 12(4): 521–6.

Larsson, L., P. A. Mardh, et al. (1978). "Detection of alcohols and volatile fatty acids by head-space gas chromatography in identification of anaerobic bacteria." *J Clin Microbiol* 7(1): 23–7.

Lee, H. S., K. A. Gwee, et al. (1998). "Validation of [13C]urea breath test for Helicobacter pylori using a simple gas chromatograph-mass selective detector." *Eur J Gastroenterol Hepatol* 10(7): 569–72.

Lewis, N., E. Severin, et al. (2001). Trace level detection of analytes using artificial olfactometry. USA, Cyrano Sciences, Inc. (Pasadena, Calif.); California Institute of Technology (Pasadena, Calif.).

Lewis, N., E. Severin, et al. (2001). Trace level detection of analytes using artificial olfactometry. USPTO. US, Cyrano Sciences California Institute of Technology.

Manolis, A. (1983). "The diagnostic potential of breath analysis." *Clin Chem* 29(1): 5–15.

McEvoy, A., C. McDonagh, et al. (1997). "Optimisation of sol-gel-derived silica films for optical oxygen sensing." *Journal of Sol-Gel Science and Technology* 8(1–3): 1121–1125.

Montuschi, P., J. V. Collins, et al. (2000). "Exhaled 8-isoprostane as an in vivo biomarker of lung oxidative stress in patients with COPD and healthy smokers." *Am J Respir Crit Care Med* 162(3 Pt 1): 1175–7.

Montuschi, P., S. A. Kharitonov, et al. (2001). "Exhaled carbon monoxide and nitric oxide in COPD." *Chest* 120(2): 496–501.

Opekun, A. R., N. Abdalla, et al. (2002). "Urea breath testing and analysis in the primary care office." *J Fam Pract* 51(12): 1030–2.

Paredi, P., S. A. Kharitonov, et al. (2000). "Exhaled ethane, a marker of lipid peroxidation, is elevated in chronic obstructive pulmonary disease." *Am J Respir Crit Care Med* 162(2 Pt 1): 369–73.

Pauling, L., A. B. Robinson, et al. (1971). "Quantitative analysis of urine vapor and breath by gas-liquid partition chromatography." *Proc Natl Acad Sci U S A* 68(10): 2374–6.

Phillips, M. (1992). "Breath tests in medicine." *Sci Am* 267(1): 74–9.

Phillips, M. (1995). Breath collection. USPTO. US.

Phillips, M. (1997). "Method for the collection and assay of volatile organic compounds in breath." *Anal Biochem* 247(2): 272–8.

Phillips, M., R. N. Cataneo, et al. (2000). "Effect of age on the breath methylated alkane contour, a display of apparent new markers of oxidative stress." *J Lab Clin Med* 136(3): 243–9.

Phillips, M., G. A. Erickson, et al. (1995). "Volatile organic compounds in the breath of patients with schizophrenia." *J Clin Pathol* 48(5): 466–9.

Phillips, M., K. Gleeson, et al. (1999). "Volatile organic compounds in breath as markers of lung cancer: a cross-sectional study." *Lancet* 353(9168): 1930–3.

Phillips, M., J. Herrera, et al. (1999). "Variation in volatile organic compounds in the breath of normal humans." *J Chromatogr B Biomed Sci Appl* 729(1–2): 75–88.

Pons, J. L., A. Rimbault, et al. (1985). "Gas chromatographic-mass spectrometric analysis of volatile amines produced by several strains of Clostridium." *J Chromatoqr* 337(2): 213–21.

Rimbault, A., P. Niel, et al. (1986). "Headspace gas chromatographic-mass spectrometric analysis of light hydrocarbons and volatile organosulphur compounds in reduced-pressure cultures of Clostridium." *J Chromatogr* 375(1): 11–25.

Rivory, L. P., K. A. Slaviero, et al. (2001). "The erythromycin breath test for the prediction of drug clearance." *Clin Pharmacokinet* 40(3): 151–8. RYBAK, I., G. THEKKADATH, et al. (1999). A SAMPLE COLLECTION AND DETECTION SYSTEM USED FOR BREATH ANALYSIS. PCT. Canada, IDS INTELLIGENT DETECTION SYSTEMS, INC.

Satoh, K., A. Yanagida, et al. (2002). Method and apparatus for analyzing breath sample. USA, Suzuki Motor Corporation (Shizuoka, JP); Takenaka; Akira (Kyoto-fu, JP).

Sear, J. W. and H. Higham (2002). "Issues in the perioperative management of the elderly patient with cardiovascular disease." *Drugs Aging* 19(6): 429–51.

Sunshine, S., M. Steinthal, et al. (2001). Handheld Sensing Apparatus. *USPTO*. US, Cyrano Sciences, Inc.

Yu, K., T. R. Hamilton-Kemp, et al. (2000). "Volatile compounds from *Escherichia coli* O157:H7 and their absorption by strawberry fruit." *J Agric Food Chem* 48(2): 413–7.

Zechman, J. M., S. Aldinger, et al. (1986). "Characterization of pathogenic bacteria by automated headspace concentrationas chromatography." *J Chromatogr* 377: 49–57.

Zechman, J. M. and J. N. Labows, Jr. (1985). "Volatiles of Pseudomonas aeruginosa and related species by automated headspace concentration—gas chromatography." *Can J Microbiol* 31(3): 232–7.

What is claimed is:

1. A method of collecting and analyzing a human breath sample comprising at least one breath compound, comprising:

exhaling into a handheld sample collector comprising a sorbent phase, to absorb at least one breath compound;

placing the handheld sample collector in fluid communication with a breath analyzer;

transferring at least one breath compound from the sample collector into the breath analyzer for separation on a thermal desorption column;

detecting at least one compound using two or more polymer-coated surface acoustic wave sensors;

wherein the handheld sample collector is not in fluid communication with the breath analyzer during the exhaling.

2. The method of claim 1, wherein the method is performed to detect breath compounds for determining health or disease diagnosis, or for drug monitoring.

3. The method of claim 1, wherein the exhaling comprises multiple exhaled breaths into the exhaled breath collector of the handheld sample collector.

4. The method of claim 1, wherein the breath sample comprises multiple breath compounds.

5. The method of claim 1, wherein the sorbent phase is selected from activated carbon, silica gel, activated alumina, molecular sieve carbon, molecular sieve zeolites, silicalite, AlPO$_4$, alumina, polystyrene, and combinations thereof.

6. The method of claim 1, further comprising inhaling through an air collector in the handheld sample collector.

7. The method of claim 6, wherein the inhaling through the air collector precedes the exhaling into the exhaled breath collector.

8. The method of claim 1, wherein the at least one breath compound is selected from the group consisting of alcohols, ethers, ketones, amines, aldehydes, carbonyls, carbanions, alkanes, alkenes, alkynes, aromatic hydrocarbons, polynuclear aromatics, biomolecules, sugars, isoprenes, isoprenoids, VOCs, VOAs, indoles, pyridines, fatty acids, and off-gases of a microorganism.

9. The method of claim 1, further comprising generating at least one profile from the sensor response.

10. The method of claim 9, wherein the method is used to prepare a diagnostic profile of a patient.

11. A diagnostic method comprising the method of claim 10, and further comprising making a diagnosis based on the profile.

12. The method of claim 1, wherein the two or more polymer-coated surface acoustic wave sensors are removable and/or replaceable.

* * * * *

(12) EX PARTE REEXAMINATION CERTIFICATE (6365th)
United States Patent
Talton (10) Number: US 7,153,272 C1
(45) Certificate Issued: Aug. 12, 2008

(54) METHODS OF COLLECTING AND ANALYZING HUMAN BREATH

(75) Inventor: James D. Talton, Gainesville, FL (US)

(73) Assignee: Nanotherapeutics, Inc., Alachua, FL (US)

Reexamination Request:
No. 90/008,706, Jul. 24, 2007

Reexamination Certificate for:
Patent No.: 7,153,272
Issued: Dec. 26, 2006
Appl. No.: 10/502,950
Filed: Nov. 18, 2004

(22) PCT Filed: Jan. 29, 2003

(86) PCT No.: PCT/US03/01065

§ 371 (c)(1),
(2), (4) Date: Nov. 18, 2004

(87) PCT Pub. No.: WO03/064994

PCT Pub. Date: Aug. 7, 2003

Related U.S. Application Data
(60) Provisional application No. 60/352,322, filed on Jan. 29, 2002.

(51) Int. Cl.
*A61B 5/08* (2006.01)

(52) U.S. Cl. ........................................ 600/543; 600/532

(58) Field of Classification Search ........................ None
See application file for complete search history.

(56) References Cited

U.S. PATENT DOCUMENTS 5,081,871 A * 1/1992 Glaser ...................... 73/863.23
6,244,096 B1 * 6/2001 Lewis et al. ................... 73/23.2

FOREIGN PATENT DOCUMENTS

WO    WO 99/20177    4/1999

OTHER PUBLICATIONS

Groves et al., "Analyzing organic vapors in exhaled breath using a surface acoustic wave sensor array with preconcentrator: Selection and characterization of the preconcentrator adsobent," *Anal. Chim. Acta.* 371:131–143 (1998) (Exhibit D).

* cited by examiner

*Primary Examiner*—Jeanne M. Clark (57) ABSTRACT

The present invention provides methods of collecting and detecting compounds in a human breath sample, comprising: exhaling into a handheld sample collector to absorb at least one breath compound in an exhaled breath collector of said collector; connecting the handheld sample collector to a breath analyzer; transferring the breath compounds from the exhaled breath collector of the sample collector into the breath analyzer; and detecting breath compounds using two or more sensors. The method may be performed to detect breath compounds for determining health or disease diagnosis, or for drug monitoring.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–12 are cancelled.

* * * * *